United States Patent
Takeno

(10) Patent No.: US 10,422,758 B2
(45) Date of Patent: Sep. 24, 2019

(54) COMPOSITION ANALYSIS METHOD AND COMPOSITION ANALYSIS SYSTEM

(71) Applicant: TOSHIBA MEMORY CORPORATION, Minato-ku, Tokyo (JP)

(72) Inventor: Shiro Takeno, Yokkaichi Mie (JP)

(73) Assignee: TOSHIBA MEMORY CORPORATION, Tokyo (JP)

(*) Notice: Subject to any disclaimer, the term of this patent is extended or adjusted under 35 U.S.C. 154(b) by 0 days.

(21) Appl. No.: 15/449,671

(22) Filed: Mar. 3, 2017

(65) Prior Publication Data
US 2018/0080886 A1 Mar. 22, 2018

(30) Foreign Application Priority Data
Sep. 16, 2016 (JP) .................. 2016-181822

(51) Int. Cl.
*G01N 23/2257* (2018.01)

(52) U.S. Cl.
CPC .............. *G01N 23/2257* (2013.01)

(58) Field of Classification Search
USPC ................. 250/306, 307, 310, 311
See application file for complete search history.

(56) References Cited

U.S. PATENT DOCUMENTS

| | | | | |
|---|---|---|---|---|
| 4,559,450 A * | 12/1985 | Robinson | ............. | G01N 23/203 250/307 |
| 5,770,861 A | 6/1998 | Hirose et al. | | |
| 6,434,217 B1 * | 8/2002 | Pickelsimer | ......... | G01B 15/025 378/89 |
| 7,358,494 B1 * | 4/2008 | Gao | ..................... | G01N 23/227 250/288 |
| 2011/0031215 A1 * | 2/2011 | Mantz | ................ | G01N 23/2252 216/60 |
| 2013/0228683 A1 * | 9/2013 | Boughorbel | ......... | G01N 23/225 250/307 |
| 2015/0012229 A1 | 1/2015 | Shishido et al. | | |
| 2016/0093468 A1 * | 3/2016 | Lang | ..................... | H01J 37/304 216/59 |

FOREIGN PATENT DOCUMENTS

| | | |
|---|---|---|
| JP | S63-237344 A | 10/1988 |
| JP | H03-251760 A | 11/1991 |
| JP | H09-115861 A | 5/1997 |
| JP | 2004-022318 A | 1/2004 |
| JP | 2014-074649 A | 4/2014 |
| JP | 2015-011018 A | 1/2015 |

* cited by examiner

*Primary Examiner* — Kiet T Nguyen
(74) *Attorney, Agent, or Firm* — Foley & Lardner LLP

(57) ABSTRACT

A composition analysis method includes iteratively irradiating a sample with an ion beam, irradiating a specific portion of the sample that is thinned by the irradiation of the ion beam with an electron beam, and detecting an intensity of an X-ray generated from the sample by the irradiation of the electron beam. The method further includes determining an identity of an element included in the sample based on at least one detection result obtained in the iterative process.

11 Claims, 5 Drawing Sheets

COMPOSITION ANALYSIS METHOD AND COMPOSITION ANALYSIS SYSTEM

CROSS-REFERENCE TO RELATED APPLICATION

This application claims the benefit of and priority to Japanese Patent Application No. 2016-181822, filed Sep. 16, 2016, the entire contents of which are incorporated herein by reference.

FIELD

Embodiments described herein relate generally to a composition analysis method and a composition analysis system.

BACKGROUND

In some semiconductor devices, a small change in a composition of components of the device may cause changes in device characteristics. Therefore, it may be useful to manufacture a semiconductor device with a specified composition. In order to evaluate a semiconductor device, composition analysis in a minute region may be helpful.

DETAILED DESCRIPTION

Some example embodiments provide for a composition analysis method and/or a composition analysis system capable of performing composition analysis in a minute region of, for example, a semiconductor device.

In general, according to some embodiments, there is provided a composition analysis method including: irradiating a sample with an ion beam; irradiating a specific portion of the sample that is thinned by the irradiation of the ion beam with an electron beam; detecting an intensity of an X-ray generated from the sample by the irradiation of the electron beam; and analyzing composition of an element included in the sample based on a result obtained by repeating the irradiation of the ion beam, the irradiation of the electron beam, and the detection of the intensity of an X-ray.

Hereinafter, some example embodiments of the present disclosure will be described with reference to the drawings. Example embodiments are not limited to the those described in present disclosure.

First Aspect

Figure 1:
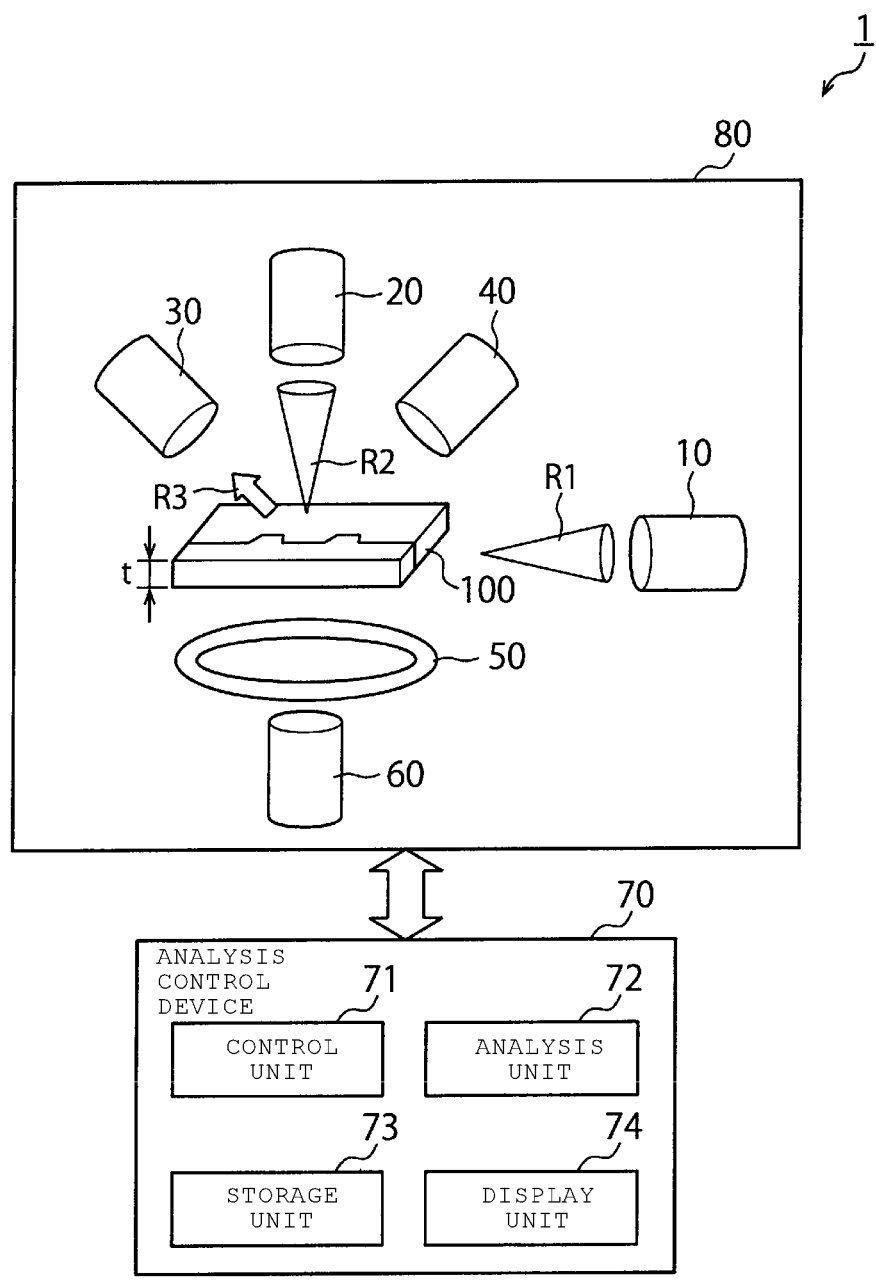
FIG. 1 is a schematic diagram showing a schematic configuration of some embodiments of a composition analysis system according to a first aspect.

FIG. 1 is a schematic diagram showing a schematic configuration of some embodiments of a composition analysis system according to a first aspect. As shown in FIG. 1, some embodiments of a composition analysis system 1 according to the first aspect includes an ion beam irradiation device 10, an electron beam irradiation device 20, an X-ray detector 30, electron detectors 40, 50, and 60, and an analysis control device 70. In the composition analysis system 1, components other than the analysis control device 70 can be disposed within a chamber 80.

The ion beam irradiation device 10 irradiates a sample 100 from a side of the sample 100 on which an ion beam R1 is incident. The sample 100 is milled by the irradiation of the ion beam R1. Therefore, the thickness t of the sample 100 becomes smaller.

In some embodiments according to the first aspect, the sample 100 is disposed on a stage (not shown). In addition, for example, the sample 100 is a semiconductor component or device. A thin film such as an oxynitride film, a metal electrode film, and a dielectric film is included in the semiconductor component. In some embodiments, a target region for composition analysis of a semiconductor component is set to a minute region of such a thin film.

For example, the electron beam irradiation device 20 irradiates the sample 100 with an electron beam R2 incident from above the sample 100, and can perform a transmission electron microscope function. In some embodiments, the electron beam irradiation device 20 irradiates the sample 100 with an electron beam R2 incident from a direction substantially orthogonal to a direction in which the ion beam R1 irradiates the sample 100. In some embodiments, the electron beam irradiation device 20 irradiates, with the electron beam R2, a specific portion of the sample 100 that was previously or is concurrently thinned by the ion beam of the ion beam irradiation device 10. The specific portion is a portion within the minute region. An X-ray R3 is emitted from the sample 100 by the irradiation of the electron beam R2.

The X-ray detector 30 detects an intensity of the X-ray R3 emitted by the sample 100. The X-ray detector 30 may be positioned above the sample 100 and may detect an intensity of an X-ray R3 emitted upward from the sample 100. Then, the X-ray detector 30 outputs a detected result to the analysis control device 70. The intensity of the X-ray R3 detected in the X-ray detector 30 can correspond to an amount of an element, and energy of the X-ray R3 can correspond to a type of the element.

The electron detector 40 detects electrons emitted from the sample 100 by the irradiation of the ion beam R1. The electron detector 40 can be positioned above the sample 100 and can detect electrons emitted upward from the sample 100. According to a detected result of the electron detector 40, it is possible to determine an irradiation result of the ion beam R1 on the sample 100. That is, by using the electron detector 40, it is possible to determine an irradiation position of the ion beam R1 with respect to the sample 100.

The electron detector 50 is disposed below the sample 100, and detects electrons transmitted through the sample 100, and more specifically, can detect an electron wave scattered in a certain angular range at the time of the irradiation of the electron beam R2. In some embodiments, a shape of the electron detector 50 is circular or annular. A likelihood of an electron scattering event occurring at a particular scattering angle may be correlated to a mass (e.g. an atomic number) of an element present in the sample 100. For example, the electron beam R2 can be strongly scattered by heavier elements at certain ranges of scattering angle.

The electron detector 60 is disposed at a position below the sample 100 and can face the sample 100 through an inner space defined by the annular electron detector 50. The electron detector 60 also detects the electrons transmitted through the sample 100 at the time of the irradiation of the electron beam R2. Therefore, according to a detected result of the electron detector 50 and/or electron detector 60, it is possible to observe various kinds of elements with a suitable contrast. By forming an image based on the detected electrons, it is possible to determine a structure of the sample 100.

For example, the analysis control device 70 may include, or may be implemented with, a personal computer including a central processing unit (CPU) and an associated memory. For example, the analysis control device 70 includes a control unit 71, an analysis unit 72, a storage unit 73, and a display unit 74.

The control unit 71 can include one or more applications, services, routines, servers, daemons, or other executable logics for controlling the ion beam irradiation device 10, the electron beam irradiation device 20, the X-ray detector 30, and the electron detectors 40 to 60. The analysis unit 72 can include one or more applications, services, routines, servers, daemons, or other executable logics for analyzing a composition of a component in a minute region of the sample 100 based on the intensity of the X-ray R3 detected by the X-ray detector 30. For example, the control unit 71 and the analysis unit 72 are configured by a CPU operated according to a predetermined program.

The storage unit 73 can include one or more electronic, optical, magnetic, or any other storage or transmission device capable of providing a CPU with program instructions, and can store various kinds of data. For example, the data includes detected data of the X-ray detector 30. For example, the storage unit 73 includes a semiconductor memory device. The display unit 74 displays an analysis result of the analysis unit 72. For example, the display unit 74 includes a liquid crystal display or a monitor.

Figure 2:
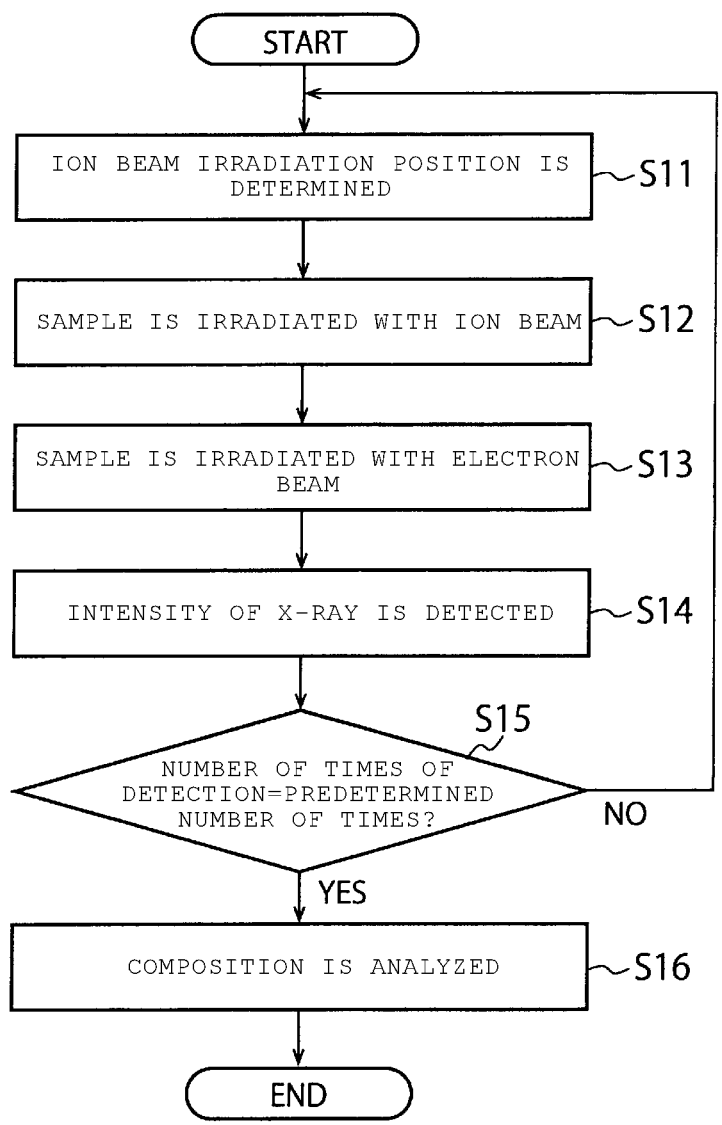
FIG. 2 is a flowchart showing a procedure of a composition analysis operation of some embodiments of a composition analysis system according to the first aspect.

Hereinafter, a procedure of some embodiments of a composition analysis operation performed by some embodiments of the composition analysis system 1 according to the first aspect will be described. FIG. 2 is a flowchart showing a procedure of the composition analysis operation performed by the composition analysis system 1.

First, the control unit 71 determines the irradiation position of the ion beam R1 with respect to the sample 100 (step S11). In other words, in step S11, the control unit 71 determines a position of the sample 100 relative to the ion beam irradiation device 10.

Next, the ion beam irradiation device 10 irradiates the sample 100 with the ion beam R1 under the control of the control unit 71 (step S12). With this, the thickness t of the sample 100 decreases. In addition, in step S12, the electron detector 40 detects one or more electrons emitted from the sample 100.

The electron beam irradiation device 20 irradiates a specific portion of the sample 100 with the electron beam R2 (step S13). In step S13, the control unit 71 sets an irradiation position of the electron beam R2 with respect to the sample 100 within a region that was thinned by the irradiation of the ion beam R1. At that time, the control unit 71 may adjust the irradiation position of the electron beam R2 based on a detected result of the electron detector 40.

The X-ray detector 30 detects the intensity of the X-ray R3 generated from the sample 100 by the irradiation of the electron beam R2 under the control of the control unit 71 (step S14). Furthermore, the X-ray detector 30 outputs detected data to the analysis control device 70. The detected data is stored in the storage unit 73.

In step S14, the electron detector 50 and the electron detector 60 detect the electron wave transmitted through the sample 100 by the irradiation of the electron beam R2 under the control of the control unit 71. The detected data is also stored in the storage unit 73.

Next, the control unit 71 determines whether or not the number of times the X-ray detector 30 implemented a detection operation to detect the intensity of the X-ray R3 is equal to a predetermined number of times (step S15). In a case where the number of times detection was performed does not equal the predetermined number of times (e.g. is less than the predetermined number of times), the control unit 71 controls the ion beam irradiation device 10, the electron beam irradiation device 20, and the X-ray detector 30 to sequentially repeat steps S11 to S14 described above.

Figure 3:
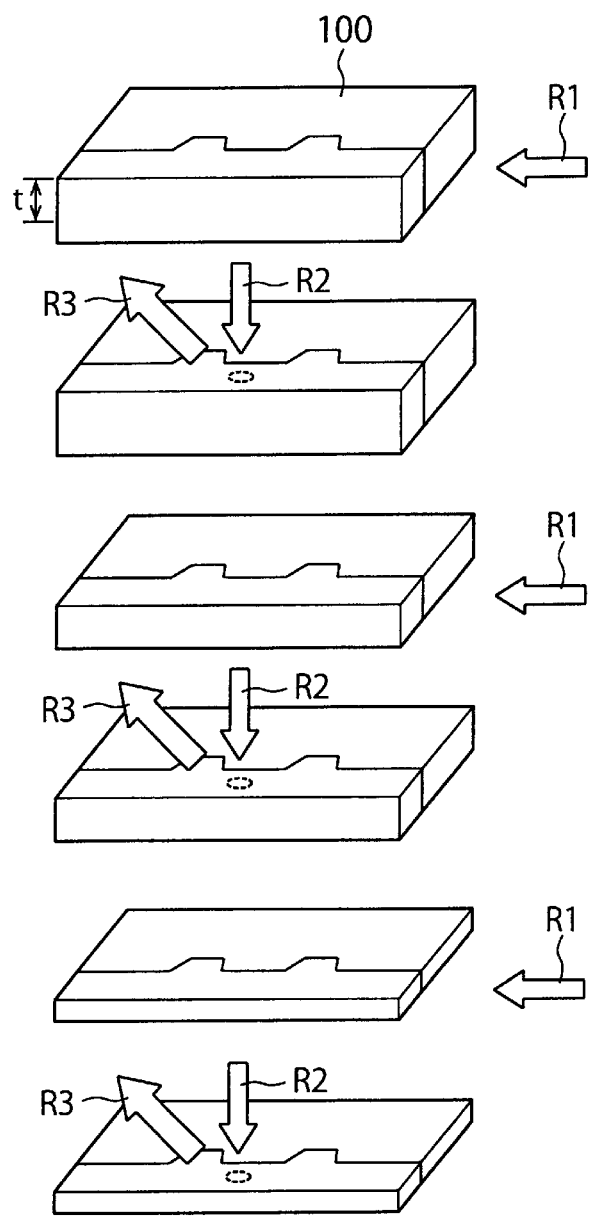
FIG. 3 is a schematic diagram showing a change in shape of a sample when irradiation of an ion beam is repeated.

FIG. 3 is a schematic diagram showing a change in shape of the sample 100 when the irradiation of the ion beam R1 is repeated. When the ion beam irradiation device 10 repeats the irradiation of the ion beam R1 on the sample 100, the thickness t of the sample 100 decreases step by step. FIG. 3 shows the thickness t becoming smaller with each iteration of an irradiation process. The sample 100 may irradiated with the ion beam R1 after a position of the ion beam irradiation device 10 or a position of the sample 100 is adjusted by the control unit 71 (e.g. to focus irradiation on a particular portion of the sample 100).

When the thickness t of the sample 100 is decreased by the irradiation of the ion beam R1, the electron beam irradiation device 20 irradiates the sample 100 with the electron beam R2. At this time, the irradiation position on the plane of the sample 100 is the same as the irradiation position on the plane in the previous irradiation. Whenever the electron beam irradiation device 20 irradiates the sample 100 with the electron beam R2, the X-ray detector 30 detects the intensity of the X-ray R3, and outputs the detected result to the analysis control device 70. As a result, detected data of the intensity of the X-ray R3 generated at the time of changing the thickness t in the minute region of the sample 100 is stored in the storage unit 73 of the analysis control device 70.

Figure 4:
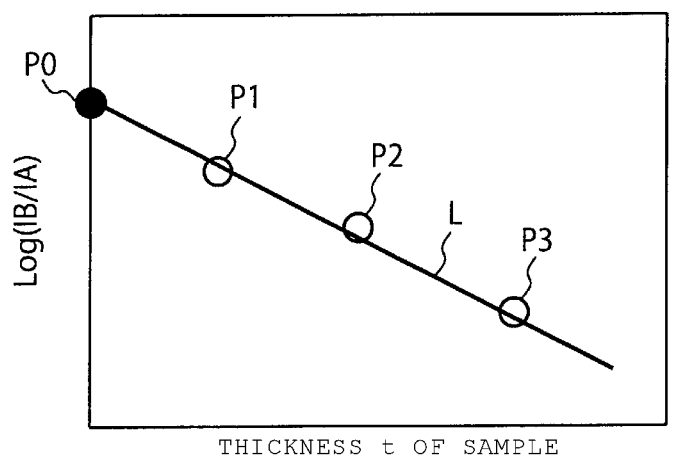
FIG. 4 is a graph showing an extrapolation of analysis data according to some embodiments of an analysis process.

Then, when the number of times a detection operation was performed reaches a predetermined number, the analysis unit 72 of the analysis control device 70 analyzes a composition of the sample 100 based on the detected data stored in the storage unit 73 (step S16) (e.g. determines the identity of a particular element type included in the sample 100). In some embodiments, the analysis unit 72 analyzes the composition of the component by using an extrapolation method. Hereinafter, the extrapolation method will be described with reference to a graph of FIG. 4. FIG. 4 is a graph showing an extrapolation of analysis data according to some embodiments of an analysis process.

Here, a case where the sample 100 includes an element A and an element B is described. In FIG. 4, a horizontal axis indicates the thickness t of the sample 100. A vertical axis indicates Log (IB/IA) obtained by taking the logarithm of a ratio of X-ray intensity IA of a particular element A and X-ray intensity IB of a particular element B.

First, the analysis unit 72 calculates Log (IB/IA) by using the detected data stored in the storage unit 73 (e.g. detected data tending to show detections of two distinct intensities). As shown in FIG. 4, the Log (IB/IA) for multiple points of data can be correlated with the thickness t of the sample 100 to generate data points P1, P2 and P3.

Next, the analysis unit 72 calculates an equation of an approximate straight line L by approximating the numeric data by, for example, the least squares method. The analysis unit 72 obtains an intercept P0 of the approximate straight line L. A value of the intercept P0 can be used to determine an absorption correction (e.g. can be used to determine an absorption correction factor that can account for absorption of X-rays in sample analysis performed using the composition analysis system 1). A value of the intercept P0 can correspond to an intensity ratio of an X-ray that is absorbed, and can be corrected for. By using the intensity ratio of a detected X-ray, it is possible to analyze a composition of a component that includes the element A and the element B with high accuracy in the minute region of the sample 100.

When the analysis of the analysis unit 72 is completed, the display unit 74 displays an analyzed result thereof. For example, the display unit 74 displays a graph and the value of the intercept P0 (intensity ratio of an X-ray that is absorbed, and can be corrected for) shown in FIG. 4. However, a display format of the display unit 74 is not particularly limited.

The intensity ratio of the X-ray using the above-described extrapolation method can also be obtained by a method in which regions having different thicknesses on the sample 100 are formed in advance, and intensity of an X-ray for each region is detected. However, this method involves a wide detection region, and thus it may be difficult to perform the composition analysis in the minute region.

Meanwhile, according to the above-described embodiment, the thickness t of the sample 100 is decreased step by step by the irradiation of the ion beam R1. Whenever the thickness is decreased, the same position on the plane of the sample 100 is irradiated with the electron beam R2 and the intensity of the X-ray R3 emitted from the sample 100 is detected. Therefore, even though the regions having different thicknesses on the sample 100 are not formed in advance, it is possible to detect an X-ray intensity corresponding to different thicknesses of the sample 100. With this, the composition of a minute region of a component can be analyzed.

Second Aspect

Figure 5:
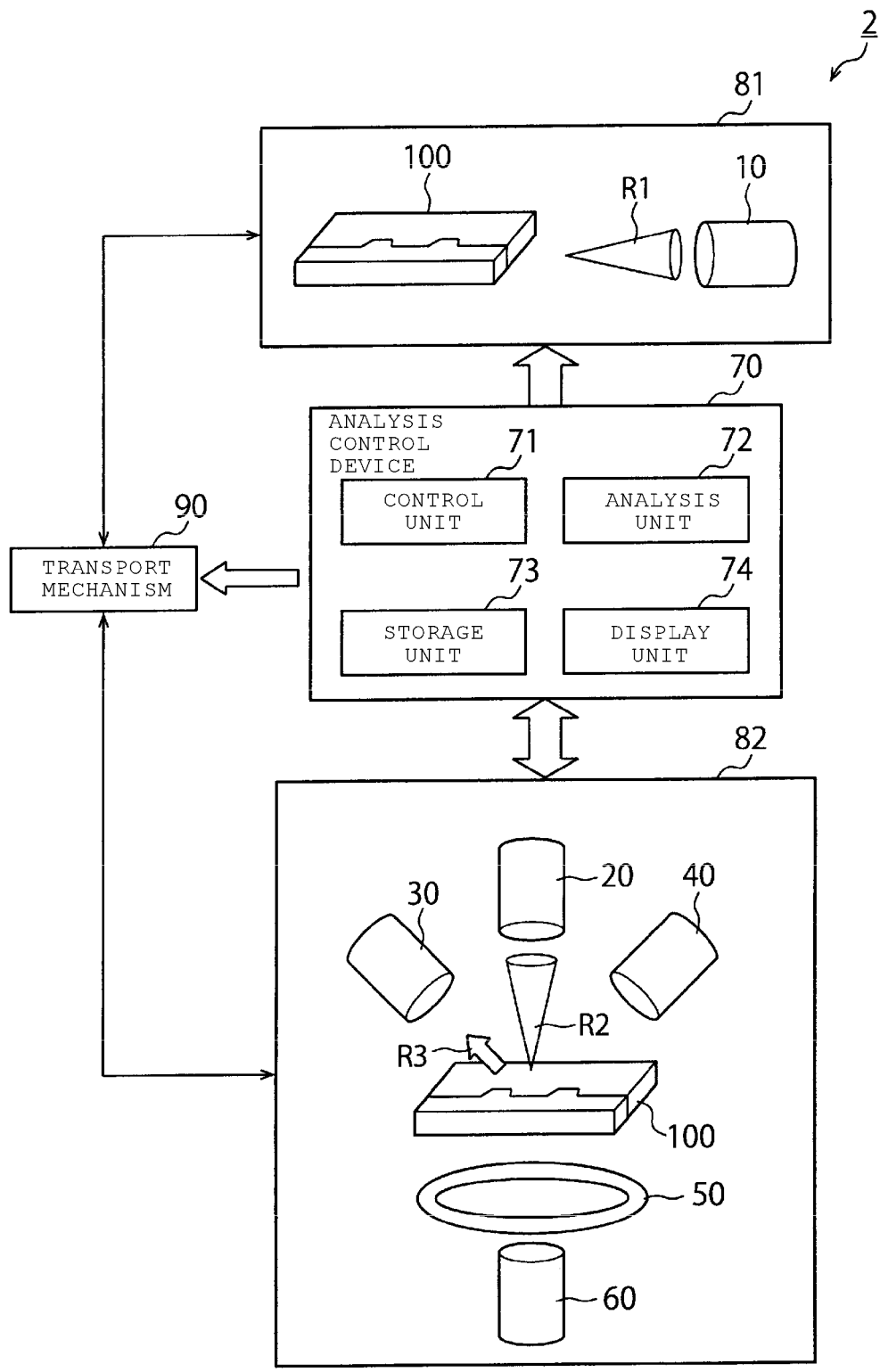
FIG. 5 is a schematic diagram showing a schematic configuration of some embodiments of a composition analysis system according to a second aspect.

FIG. 5 is a schematic diagram showing some embodiments of a schematic configuration of a composition analysis system according to a second aspect. In FIG. 5, components similar to those described above are denoted by same reference numerals, and a detailed description thereof will be omitted.

In the composition analysis system 1 according to the first aspect, the ion beam irradiation device 10, the electron beam irradiation device 20, and the X-ray detector are disposed within the chamber 80. Therefore, the irradiation of the ion beam R1, the irradiation of the electron beam R2, and detection of the intensity of the X-ray R3 are performed at a same location.

Meanwhile, in some embodiments of a composition analysis system 2 according to the second aspect, as shown in FIG. 5, the ion beam irradiation device 10 is disposed within a chamber 81, but the electron beam irradiation device 20, the X-ray detector 30, and the electron detectors 40 to 60 are disposed within a chamber 82. Therefore, the irradiation of the ion beam R1 is performed within the chamber 81, and the irradiation of the electron beam R2 and the detection of the intensity of the X-ray R3 are performed within the chamber 82.

In addition, in some embodiments, a transport mechanism 90 transports the sample 100 between the chamber 81 and the chamber 82 under the control of, for example, the control unit 71. Specifically, when the irradiation of the ion beam R1 is completed, the transport mechanism 90 transports the sample 100 from the chamber 81 to the chamber 82.

Subsequently, when the irradiation of the electron beam R2 and the detection of the intensity of the X-ray R3 are completed, the transport mechanism 90 returns the sample 100 from the chamber 82 to the chamber 81. In this manner, the irradiation of the ion beam R1, and the irradiation of the electron beam R2 and the detection of the intensity of the X-ray R3 are repeated at different locations. Additionally or alternatively, methods other than use of the transport mechanism 90 may be implemented to transport the sample 100 between chambers, such as having a person carry the sample 100.

Also in the above-described embodiment, similarly to the first embodiment, the thickness t of the sample 100 is decreased step by step by the irradiation of the ion beam R1. Whenever the thickness is decreased, the same position on the plane of the sample 100 is irradiated with the electron beam R2, and the intensity of the X-ray R3 emitted from the sample 100 is detected. With this, the composition of a minute region of a component can be analyzed.

According to some embodiments, for example, even in a case where it is difficult to install a processing device (ion beam irradiation device 10), and a measurement device (electron beam irradiation device 20 and X-ray detector 30) in the same chamber, it is possible to analyze the composition of the element in the minute region.

In embodiments according to the first aspect and the second aspect, a spherical aberration correction technique maybe applied to the electron beam irradiation device 20. In this case, a size of an irradiation region of the electron beam R2 in the sample 100 further decreases. Therefore, it is possible to further miniaturize an analysis area.

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of embodiments of this disclosure are not deviated from by such arrangement.

In the description of some embodiments, orthogonal or substantially orthogonal can refer to a range of angular variation about 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

While certain embodiments have been described, these embodiments have been presented by way of example only, and are not intended to limit the scope of the present disclosure. Indeed, the embodiments described herein may be embodied in a variety of other forms; furthermore, various omissions, substitutions and changes in the form of the embodiments described herein may be made without departing from the spirit of the present disclosure. The accompanying claims and their equivalents are intended to cover such forms or modifications as would fall within the scope and spirit of the present disclosure. Moreover, some or all of the above described embodiments can be combined when implemented.

What is claimed is:
1. A composition analysis method comprising:
  determining a plurality of intensities by iteratively performing a process of:
    irradiating a sample with an ion beam;

determining a thickness of a specific portion of the sample that is thinned by the irradiation of the ion beam;

irradiating the specific portion of the sample that is thinned by the irradiation of the ion beam with an electron beam; and detecting an intensity of an X-ray generated from the sample by the irradiation of the electron beam, the intensity including at least a first intensity corresponding to a first element and a second intensity corresponding to a second element;

determining a plurality of parameter values based on a ratio of the first intensity and the second intensity included in the determined plurality of intensities;

determining a first linear function based on a correlation between the determined plurality of parameter values and the determined thickness using an extrapolation method;

determining a calculated parameter value which corresponds to a theoretical point where the thickness becomes zero; and performing a composition analysis using the calculated parameter value.

2. The method according to claim 1,
wherein the irradiation of the ion beam, the irradiation of the electron beam, and the detection of the intensity of the X-ray are performed in a same location.

3. The method according to claim 1,
wherein at least two of the irradiation of the ion beam, the irradiation of the electron beam, and the detection of the intensity of the X-ray are performed in different locations.

4. The method according to claim 1,
wherein the iterative process is repeated a predetermined number of times, and then the determining the identity of the element included in the sample is performed.

5. The method according to claim 1, wherein:
the sample is irradiated with the ion beam from a first direction, and
the sample is irradiated with the electron beam from a second direction different from the first direction.

6. The method according to claim 1, further comprising:
detecting an electron transmitted through the sample at the time of the irradiation of the electron beam.

7. The method according to claim 1, wherein the calculated parameter value is a P0-intercept of the first linear function.

8. The method according to claim 7, further comprising determining an absorption correction factor based on the P0-intercept.

9. A composition analysis system comprising:
an ion beam irradiation device configured to irradiate a sample with an ion beam;
an electron beam irradiation device configured to irradiate a specific portion of the sample that is thinned by the irradiation of the ion beam with an electron beam;
an X-ray detector configured to detect an intensity of an X-ray generated from the sample by the irradiation of the electron beam; and
an analysis control device configured to control the ion beam irradiation device, the electron beam irradiation device, and the X-ray detector to:
determine a plurality of intensities by iteratively performing a process of:
irradiating the sample with the ion beam;
determining a thickness of the specific portion of the sample that is thinned by the irradiation of the ion beam;
irradiating the specific portion of the sample that is thinned by the irradiation of the ion beam with the electron beam; and
detecting the intensity of the X-ray generated from the sample by the irradiation of the electron beam, the intensity including at least a first intensity corresponding to a first element and a second intensity corresponding to a second element;
determine a plurality of parameter values based on a ratio of the first intensity and the second intensity included in the determined plurality of intensities;
determine a first linear function based on a correlation between the determined plurality of parameter values and the determined thickness using an extrapolation method;
determine a calculated parameter value which corresponds to a theoretical point where the thickness becomes zero; and
perform a composition analysis using the calculated parameter value.

10. The system according to claim 9, wherein the calculated parameter value is a P0-intercept of the first linear function.

11. The system according to claim 10, wherein the analysis control device is further configured to determine an absorption correction factor based on the P0-intercept.

* * * * *